(12) United States Patent
Lockhart et al.

(10) Patent No.: US 6,226,547 B1
(45) Date of Patent: May 1, 2001

(54) CATHETER TRACKING SYSTEM

(75) Inventors: Peter Lockhart; James Alexander Rex, both of Hants (GB)

(73) Assignee: Roke Manor Research Limited, Hants (GB)

(\*) Notice: Subject to any disclaimer, the term of this patent is extended or adjusted under 35 U.S.C. 154(b) by 0 days.

(21) Appl. No.: 09/192,217

(22) Filed: Nov. 16, 1998

(30) Foreign Application Priority Data

Nov. 15, 1997 (GB) .................................... 9724073

(51) Int. Cl.[7] .................................................. A61H 5/05

(52) U.S. Cl. .................... 600/424; 600/429; 324/207.12; 324/207.17

(58) Field of Search .................................. 600/407, 424, 600/409, 421, 422, 423, 429; 324/207.12, 207.17, 232; 128/653.1

(56) References Cited

U.S. PATENT DOCUMENTS 5,913,820 \* 6/1999 Bladen et al. ........................ 600/407

\* cited by examiner

*Primary Examiner*—Marvin M. Lateef
*Assistant Examiner*—Jeoyuh Lin
(74) *Attorney, Agent, or Firm*—Evenson, McKeown, Edwards & Lenahan, P.L.L.C.

(57) ABSTRACT

A catheter tracking system as depicted in FIGS. 1,2, and 3 for locating and tracking a position of a catheter head 16 within a part of a human or animal body 1. The catheter tracking system including of a catheter 10 having a head 16 which is arranged to be conveyed through a human or animal body to a desired location, a plurality of magnetic field transducers, at least one of which is disposed on the catheter 18, and others of which are located in/or around a body and which serve as reference transducers 19, and a control unit which energises the plurality of magnetic field transducers. Upon processing of the magnetic field signals the position of a catheter head 16 with respect to reference transducers 19 is determined.

7 Claims, 3 Drawing Sheets

CATHETER TRACKING SYSTEM

The present invention relates to catheter tracking systems which serve to determine a position of catheters within the human or animal body. Furthermore, the present invention relates to methods for tracking catheters within the human or animal body.

The term catheter as used herein refers to any type of invasive surgical tool, used for insertion into a human or animal body for the purpose of providing remote access to a part of the body for performing some type of investigative and/or medical procedure.

BACKGROUND OF THE INVENTION

With the increasing use of minimally invasive surgical techniques in medical diagnosis and therapy, there is a need for a new method of remotely locating and tracking catheters or other medical instruments inside a human or animal body. Currently, x-ray fluoroscopic imaging is the standard catheter tracking technique. However, excessive exposure to x-ray dosages by both the patient and clinician can be harmful. Thus, alternative catheter tracking methods are desirable.

Several alternative methods have been published including some which employ ultrasonic transducers and others which make use of magnetic field measurements.

One known method of catheter location employs one or more magnetic field sources, which are fixed relative to one another and define a spatial reference frame, and one or more magnetic sensors, fixed to the tip of the catheter. The sensors measure the fields produced by the sources, and these measurements are then used to determine the tip's position relative to the reference frame. The same result could alternatively be achieved with the sources replaced by sensors, and the sensors by sources.

This technique relies on accurate prior knowledge of the relative positions of the sources and the spatial forms of their magnetic fields, and of the relative positions and sensitivities of the sensors. Because it is not possible to manufacture sources and sensors with ideal characteristics, purely theoretical calculations of such characteristics are likely to be erroneous, and hence they must be determined from calibration measurements. One advantage of using magnetic fields to track a catheter inside a human or animal body is that the fields are virtually unaffected by the presence of the body. This is due to the very low magnetic susceptibility of body tissue. In contrast, electric and acoustic fields are strongly affected by body tissue. The result is that calibration measurements of a magnetic field tracking system can be made without the presence of the body, before surgery.

A limitation placed on catheters is that they must be small enough in diameter and flexible enough to allow insertion into the relevant part of the body. For example, cardiac catheter diameters should be around 2 mm, and flexible enough to bend to a radius of 10 mm or less. These requirements, and the need to fix the catheter mounted transducers rigidly together, close to the catheter head, demand that these transducers must all be contained in a small volume.

A known catheter tracking method based on the above approach is described in PCT Patent Application WO 96105768 (Ben-Haim et al). In Ben-Haim's method, there are a plurality of magnetic sources, preferably three, and a plurality of catheter mounted sensors, again preferably three. The sensors are preferably wire coils, of the type which measure the local field component parallel to its axis, aligned in orthogonal directions.

Since multiple simultaneous but independent measurements of the magnetic fields are necessary in order to perform a location, the known catheter tracking method requires that the plurality of magnetic sources and the plurality of catheter mounted sensors be arranged independently such that none of their fields can be expressed as a fixed combination of the other fields, and so that none of their measurements can be expressed as a fixed combination of the other measurements. Since a magnetic field is a vector quantity, it is possible for up to three co-located transducers to be mutually independent, provided they are fixed orthogonally with respect to one another. More than three transducers must be spatially separated, in order to be mutually independent.

Known catheter location method suffers from certain disadvantages. Firstly, three magnetic field coils, arranged independently, must be integrated into a small volume near the head of the catheter. This represents a difficult and costly procedure. Secondly, calibration of the sensors in each catheter is a complex procedure, especially measuring their orientations. Factory calibration is thus preferable to calibration of each catheter just prior to use by the medical personnel. However, if the catheters are calibrated in advance, a fool-proof system will be needed to ensure that the correct calibration data for each catheter is entered into the signal processor.

The aforementioned disadvantages associated with calibration, independence of magnetic field transducers, and size of a catheter head, represent technical problems addressed by the catheter tracking system according to the present invention.

SUMMARY OF THE INVENTION

The invention proposed here employs just one magnetic field transducer mounted proximate a catheter head of a catheter to be tracked.

According to the present invention there is provided a catheter tracking system for determining the location and orientation of the tip of a catheter, said tracking system comprising a plurality of magnetic field transducers and a control unit coupled to said plurality of magnetic field transducers and arranged to energise said plurality of magnetic field transducers to generate or detect magnetic fields, characterised in that one of said plurality of magnetic field transducers is disposed on said catheter proximate the distal end thereof, and others of said plurality of magnetic field transducers are disposed at reference positions with respect to each other, and arranged to be substantially independent, and consequent upon detection of magnetic fields generated by selected ones of said plurality of transducers, said control unit operates to process detected signals representative of said detected magnetic fields, to determine three location co-ordinates and two orientation co-ordinates of said catheter with respect to a reference frame defined by said reference transducers.

According to an aspect of the present invention there is provided a method of tracking a catheter for determining the location and orientation of a catheter, said method comprising the steps of disposing a single magnetic field transducer on said catheter proximate the distal end thereof and energising said single magnetic field transducer to operate as either a magnetic field generator or magnetic field detector, inserting said catheter into a human or animal body, disposing a plurality of other magnetic field transducers at reference positions, with respect to each other, in or around said human or animal body, and arranged to be substantially independent, and energising said plurality of other magnetic field transducers to operate as either magnetic field generators or magnetic field detectors, thereby creating a reference frame around said human or animal body, and processing detected signals representative of said detected magnetic fields, to determine three location co-ordinates and two orientation co-ordinates of said catheter, with respect to said reference frame.

The catheter tracking system proposed here offers several potential advantages over the prior art. Firstly, the present invention requires only a single transducer be disposed proximate the distal end of a catheter thus simplifying the calibration procedure for the catheter, since relative transducer positions do not need to be measured. Additionally, a single transducer disposed proximate the distal end of a catheter occupies a smaller volume and has fewer connecting wires, so it is more easily integrated into a catheter than is possible with the current systems, which require a plurality of transducers to be located on the catheter.

Advantageously, the present invention allows for the option of using a larger, more powerful magnetic field sensor located on the catheter, thus increasing the sensitivity of the sensor, which allows greater measurement accuracy for a given magnetic field strength. Similarly, if a magnetic field source is located on the catheter, the use of a more powerful source gives a greater field strength per unit drive current, thereby reducing operating current requirements.

BRIEF DESCRIPTION OF THE DRAWING

While the principle advantages and features of the invention have been described above, a greater understanding and appreciation of the invention may be obtained by referring to the drawings and detailed description of the preferred embodiment, presented by way of example only, in which.

DETAILED DESCRIPTION OF THE DRAWING

Figure 1:
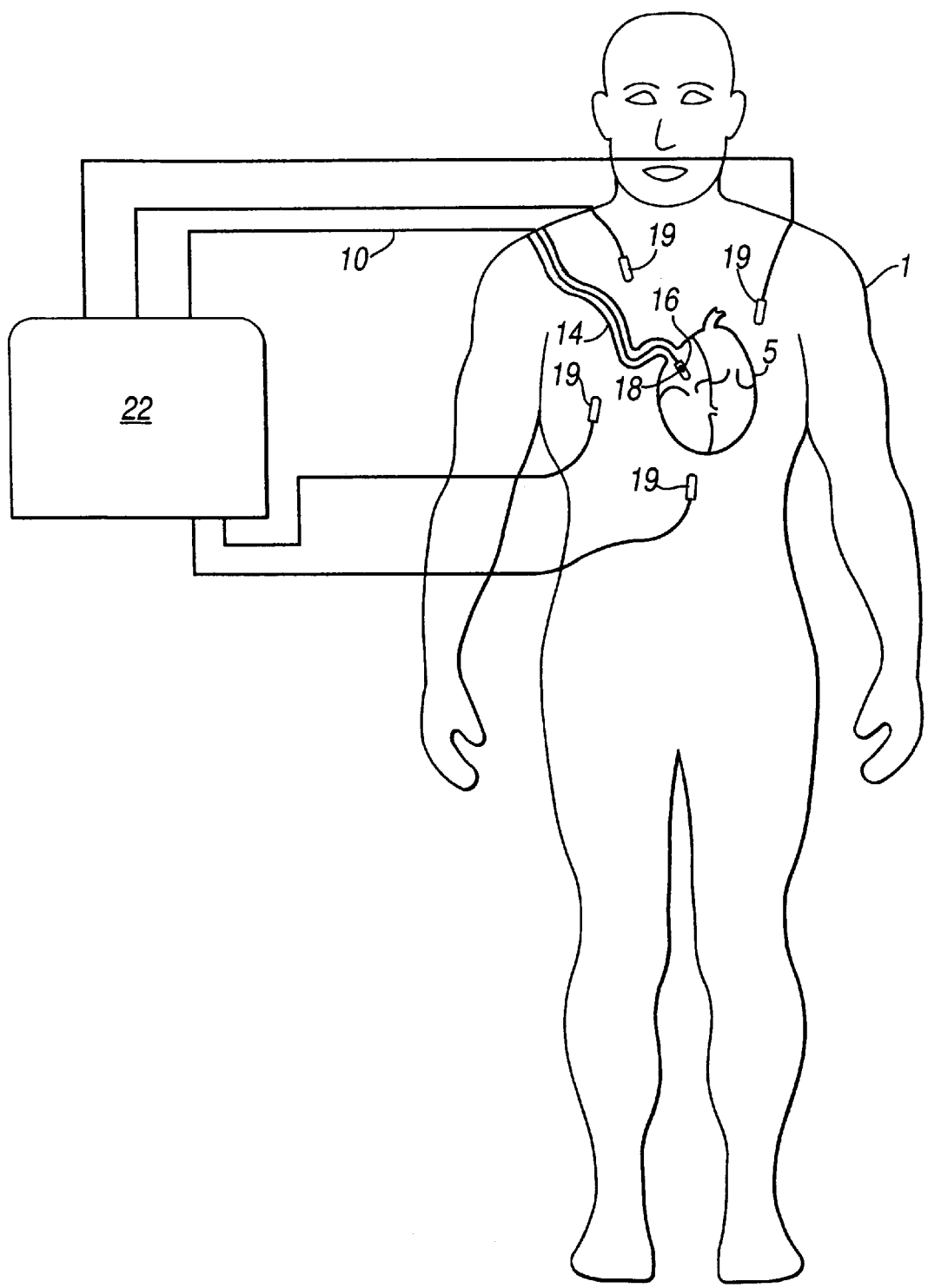
FIG. 1 is a schematic diagram of a catheter inserted in a human body.

FIG. 1 provides a schematic illustration of a catheter 10 inserted into a human body 1, through an artery 14, and into a heart 5, which is one application for the magnetic field catheter tracking system according to the present invention. The catheter 10 further comprises generally of a head 16 upon which is disposed a magnetic field transducer 18. A plurality of other magnetic field transducers 19 are disposed near the heart 5 at fixed reference positions, held in place by a rigid frame (not shown). These reference transducers 19 are arranged to be substantially independent, such that in the case of magnetic field sources none of their fields can be expressed as a fixed combination of the other fields, and in the case of magnetic field sensors, that none of their measurements can be expressed as a fixed combination of the other measurements. The reference transducers 19 and the magnetic field transducer 18 are connected to a signal processing unit 22. In use, the catheter 10 is inserted into a human body 1, via a vein or artery 14, to gain remote access to for example the heart 5, for the purpose of performing some type of medical procedure, for example endocardiography.

In this example embodiment, the catheter mounted magnetic field transducer 18 is a magnetic field sensor, in which case the reference transducers 19 are magnetic field sources. In FIG. 1, the reference transducers 19 are coil type transducers, however other types could be employed. As an alternative embodiment, the catheter mounted transducer is a source, in which case the reference transducers are sensors.

For the remainder of this description of a preferred embodiment of the invention detailed herein, it is assumed that a magnetic field sensor is mounted on the catheter and that the reference transducers are magnetic field sources. However, essentially the same technique could be used with the sources replaced with sensors and vice versa.

Figure 2:
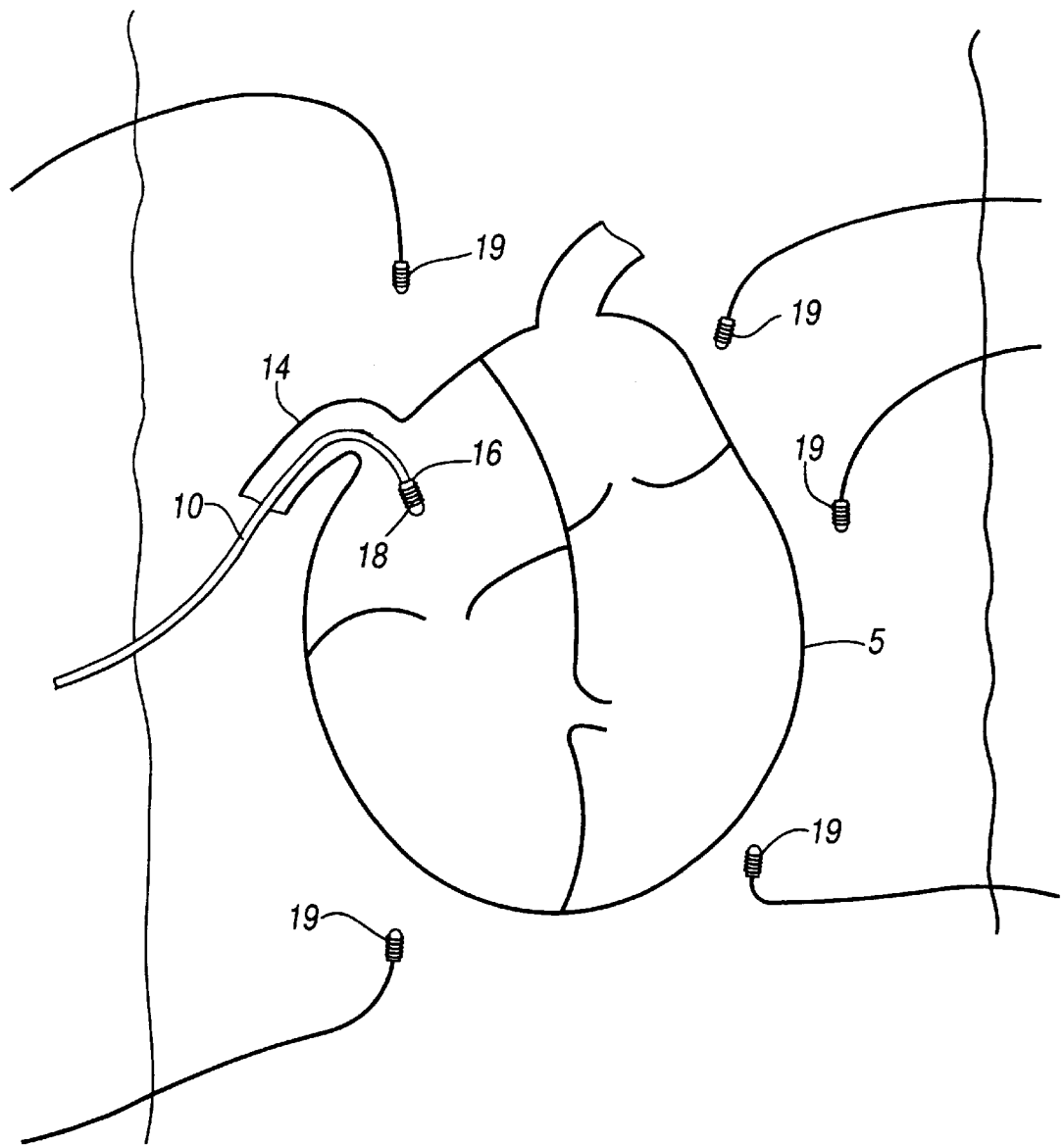
FIG. 2 shows a typical catheter inserted through an artery into a heart, with reference transducers located near the heart, and in particular one magnetic field transducer located on the head of the catheter inserted into the heart, and, FIG. 3 shows a schematic diagram of the signal processing unit, in conjunction with several reference transducers located outside the body as well as a catheter, inserted into a part of a body through an artery, with a single transducer located on the catheter head.

FIG. 2 shows a close-up of the catheter shown in FIG. 1, where parts also appearing in FIG. 1 bear identical numerical designations. A catheter 10, is shown disposed within artery 14 leading into a heart 5. Located on the head of the catheter 16 is a magnetic field transducer 18 of a coil type. Located near the heart 5 are a plurality of reference magnetic field transducers 19 of a coil type, held in place by the rigid frame (not shown).

Figure 3:
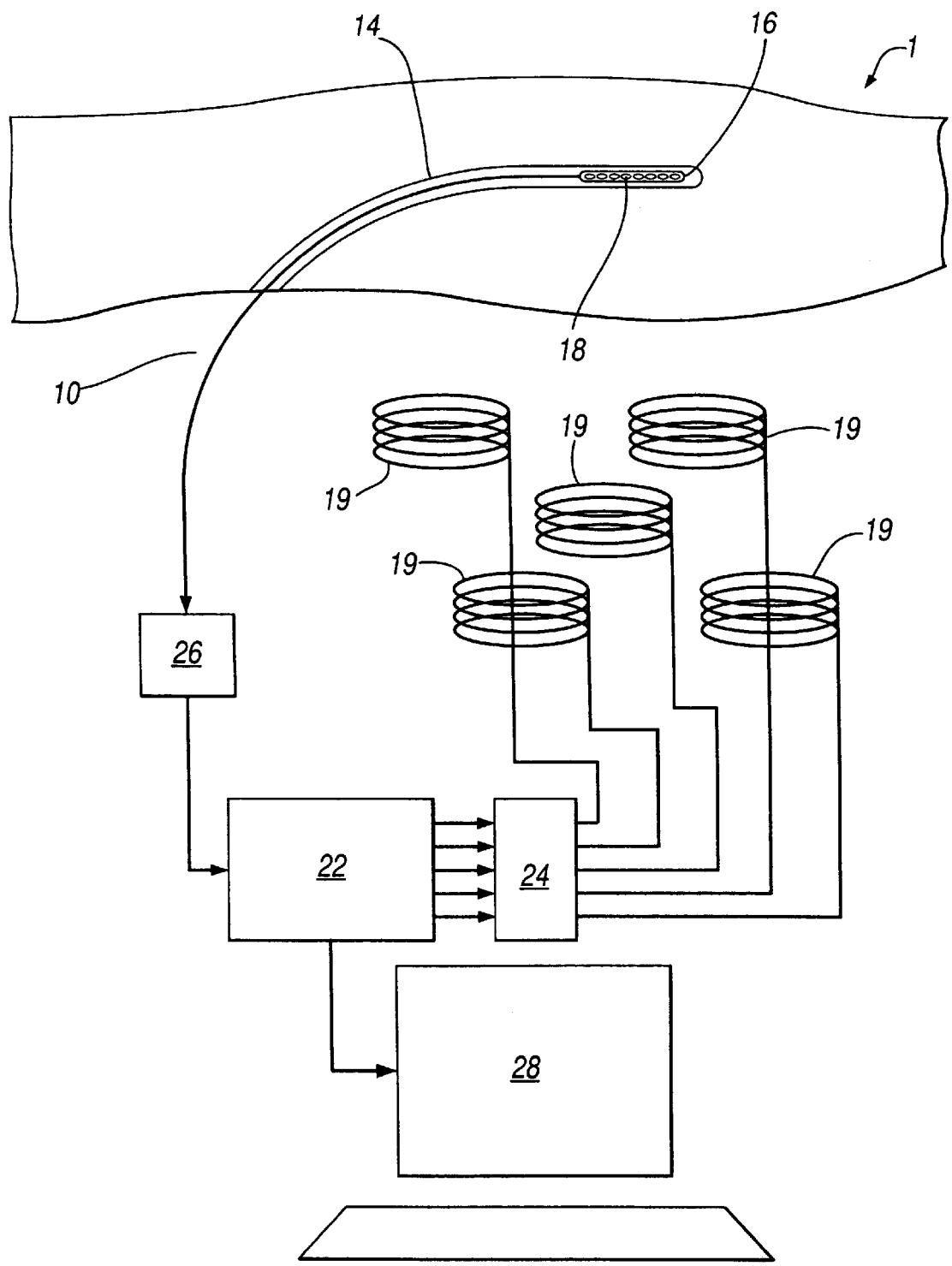

FIG. 3 shows essentially the same items as in FIG. 1, except in more detail, where parts also appearing in FIGS. 1 and 2 bear identical numerical designations. The catheter 10, with a magnetic field transducer 18 located on the catheter head 16 is inserted into a body 1, through an artery 14. In order to maintain a spatial relationship between the reference transducers, it is preferred that the reference transducers are mounted externally, outside the body on the aforementioned frame. This will provide the requisite independence of the respective magnetic fields. Thus FIG. 3 illustrates a preferred embodiment, with the reference transducers 19 located outside the body 1. Five independently arranged reference magnetic field sources 19 are attached to a multi-channel amplifier 24. A magnetic field sensor's output signal is transmitted via a catheter 10 to an amplifier 26 where it is amplified and fed into a signal processor unit 22. The signal processing unit 22 generates the drive signals which are fed to magnetic sources 19 via the multi-channel amplifier 24. Also attached to the signal processor 22 is a computer based user interface 28, which displays the catheter's head position and other results calculated by the processor, and accepts the user's commands to adjust various system parameters.

The catheter head 16 has six degrees of positional freedom, three transitional plus three rotational. To fully determine the catheter head's position preferably requires at least six independent magnetic field measurements, giving six independent equations in the six unknown positional co-ordinates. However, in most cases the angle of rotation of the catheter head 16 about its axis is not of interest, so only five positional co-ordinates need be determined, thus five field measurements are sufficient.

The N reference sources (N=five for this description of the preferred embodiment) are fixed into a rigid unit, (not shown) and arranged so that the fields generated are mutually independent functions of the spatial co-ordinates of the reference frame. The magnetic field sensor measures the directional component of the local magnetic field parallel to the catheter's axis. The sensor's output due to the nth source can thus be written as:

$$x_n(t) = k B_n(r_s, t) \cdot P_s \quad \text{(Equation 1)}$$

In Equation 1, $B_n$ (r, t) is the magnetic field vector produced by source n at time t and at the three-dimensional location r in the reference frame, $r_s$ is the sensor's location, $P_s$ is a unit vector parallel to the catheter's axis, and k is the sensor's sensitivity. Note that bold face symbols denote vector quantities and x.y denotes the scalar product of x and y. Vector $r_s$ has three degrees of freedom, but the unit vector $P_s$ has only two. This reflects the fact that the sensor's output is independent of its angle of rotation about the catheter's axis, so this angle cannot be determined. The sensor's orientation is thus defined by only two co-ordinates rather than three.

Separate measurements of the source fields are obtained by multiplexing the sources, and subsequently de-multiplexing the sensor output. This also allows for the earth's magnetic field and any other ambient noise fields can be cancelled out of the measurement. As the sensor's response is linear, frequency-division multiplexing could be used, with each field varying at a different single frequency.

At any particular catheter position, the de-multiplexed sensor measurements of the N source field will be time-independent so Equation 1 can be rewritten as:

$$x_n = kB_n(r_s) \cdot P_s \text{ for } n=1 \text{ to } N \qquad \text{(Equation 2)}$$

The functions $B_n$ (r) will be determined by calibration of the reference sources, and the constant k by calibration of the sensor. Hence, the five location and orientation co-ordinates of the sensor 18 (disposed on the catheter 10 proximate the catheter head 16) in vectors $r_s$ and $P_s$ may be found by solving these N equations, provided N is at least five.

In an alternative embodiment of the present invention, the number of reference transducers (N) is six or more, thus facilitating the determination of the sensor's sensitivity (k) from the measurement equations, thus advantageously eliminating the need to calibrate the catheter mounted sensor 18.

As the catheter 10 is manipulated by the clinician, the catheter head 16 can be tracked by continually recalculating its positional co-ordinates. In some procedures it may be useful to track more than one catheter. This can be done simply by replicating the transducer and interface electronics in each catheter, and repeating the equation solving process for each set of N field measurements.

Calibration of the reference transducers 19 could be a fairly lengthy procedure, but the reference unit can then be re-used indefinitely. Calibrating the transducer 18 disposed on the catheter will be a simple measurement. For example, it could be done just before using the catheter, by placing its head at a known position in the reference frame, using a jig attached to the reference unit.

As will be appreciated by those skilled in the art, various modifications may be made to the embodiment hereinbefore described without departing from the scope of the present invention.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A catheter tracking system for determining the location and orientation of a catheter, said tracking system comprising a plurality of magnetic field transducers and a control unit coupled to said plurality of magnetic field transducers and arranged to energize said plurality of magnetic field transducers to generate or detect magnetic fields, wherein:

one of said plurality of magnetic field transducers is disposed on said catheter proximate a distal end thereof, and others of said plurality of magnetic field transducers are disposed at reference positions with respect to each other, and arranged to be substantially independent in accordance with an external calibration method; and consequent upon detection of magnetic fields generated by selected ones of said plurality of transducers, said control unit operates to process detected signals representative of said detected magnetic fields, to determine three location co-ordinates and two orientation co-ordinates of said catheter with respect to a reference frame defined by said reference transducers.

2. A catheter tracking system as claimed in claim 1, wherein said one magnetic field transducer disposed on said catheter proximate the distal end thereof, operates as a magnetic field sensor, and said others of said plurality of transducers operate as magnetic field sources.

3. A catheter tracking system as claimed in claim 1, wherein said one magnetic field transducer disposed on said catheter proximate the distal end thereof, operates as a magnetic field source, and said others of said plurality of transducers operate as magnetic field sensors.

4. A catheter tracking system as claimed in claim 1, wherein said plurality of magnetic field transducers are coils.

5. A catheter tracking system as claimed in claim 1, wherein a magnetic field generated by each of said magnetic field sources has at least one of a frequency and a phase which differs from that of the other magnetic field sources, thereby facilitating contemporaneous generation and detection of said magnetic fields.

6. A catheter tracking system as claimed in claim 1, wherein said plurality of other magnetic field transducers are at least five transducers.

7. A method of tracking a catheter for determining the location and orientation of a catheter, said method comprising the steps of disposing a single magnetic field transducer on said catheter proximate the distal end thereof and energizing said single magnetic field transducer to operate as either a magnetic field generator or magnetic field detect, inserting said catheter into a human or animal body, disposing a plurality of other magnetic field transducers at reference positions, with respect to each other, in or around said human or animal body, and arranged to be substantially independent in accordance with an external calibration method, and energizing said plurality of other magnetic field transducers to operate as either magnetic field generators or magnetic field detectors, thereby creating a reference frame around said human or animal body, and processing detected signals representative of said detected magnetic fields, to determine three location co-ordinates and two orientation co-ordinates of said catheter, with respect to said reference frame.

\* \* \* \* \*